United States Patent

Yamaki et al.

[11] Patent Number: 5,643,244
[45] Date of Patent: Jul. 1, 1997

[54] DISPOSABLE GARMENT FOR ABSORPTION OF BODY EXUDATES

[75] Inventors: Rumi Yamaki, Kawanoe; Takaaki Shimada, Shita-gun, both of Japan

[73] Assignee: Uni-Charm Co., Ltd., Ehime, Japan

[21] Appl. No.: 557,100
[22] PCT Filed: Apr. 7, 1995
[86] PCT No.: PCT/JP95/00691
§ 371 Date: Dec. 6, 1995
§ 102(e) Date: Dec. 6, 1995
[87] PCT Pub. No.: WO95/27459
PCT Pub. Date: Oct. 19, 1995

[30] Foreign Application Priority Data

Apr. 7, 1994 [JP] Japan ...................... 6-069608

[51] Int. Cl.⁶ .................................................. A61F 13/15
[52] U.S. Cl. .................. 604/385.2; 604/373; 604/374
[58] Field of Search .............................. 604/369, 373, 604/374, 385.2

[56] References Cited

U.S. PATENT DOCUMENTS

| | | | |
|---|---|---|---|
| 4,640,859 | 2/1987 | Hanson et al. | 604/385.2 |
| 4,917,682 | 4/1990 | Lancaster et al. | 604/385.2 |
| 5,336,453 | 8/1994 | Zehner et al. | 604/370 |

FOREIGN PATENT DOCUMENTS

| | | |
|---|---|---|
| 60-136308 | 9/1985 | Japan . |
| 62-88704 | 6/1987 | Japan . |

*Primary Examiner*—Robert A. Clarke
*Attorney, Agent, or Firm*—Lowe, Price, LeBlanc & Becker

[57] ABSTRACT

There is provided a leakage barrier 10 made of a soft elastic material longitudinally extending on either side of a crotch-contacting section 9 on its inner surface, a top surface 12 of the leakage barrier 10 having a plurality of longitudinally alternate crests 13 and troughs 14 each extending longitudinally of the leakage barrier 10.

4 Claims, 2 Drawing Sheets

DISPOSABLE GARMENT FOR ABSORPTION OF BODY EXUDATES

TECHNICAL FIELD

The present invention relates to a disposable garment to be put against the wearer's crotch for absorption of body exudates, such as a disposable diaper for babies and adults, training pants for babies, and a sanitary napkin.

BACKGROUND ART

In a disposable garment to be put against the wearer's crotch for absorption of body exudates such as a disposable diaper and a sanitary napkin, it is well known to provide the garment on its inner surface destined to be put against the wearer's crotch with a leakage barrier for body exudates extending in the transversely opposite sides of the garment's crotch section longitudinally of the garment. For example, Japanese Laid-Open Utility Model Application No. Sho60-136308 discloses leakage barriers for the above-mentioned purpose comprising a relatively wide strip made of a spongy soft elastic foam bonded to an inner surface of a diaper with a preselected tension so as to extend longitudinally of opposite sides of the diaper's crotch section. According to the diaper, the respective strips of foam should swell up against the wearer's skin upon release of said tension and form the soft elastic leakage barriers. Japanese Laid-Open Utility Model Application No. Sho62-88704 also discloses a tape-like member made of polyurethane foam or the like are respectively bonded to an inner surface of a diaper on transversely opposite sides of the diaper's crotch section so that the tape-like member may present an Ω (omega)-shaped cross-section and thereby function as a desired leakage barrier. According to the diaper, it should be provided with a comfortably soft touch leakage barrier being able to follow the movements of the wearer's body and thereby to maintain a good fitness not only against the wearer's crotch but also around each leg of the wearer.

However, with the garments provided with the conventional paired leakage barriers made of a soft elastic material such as a polyurethane foam as mentioned above, the soft elastic material tends to be angularly bent at one or more locations therealong rather than describing a smooth curve and consequently to form remarkable crests extending transversely of the respective leakage barriers. The leakage barriers are prevented by these crests from being entirely brought into close contact with the wearer's skin. In other words, these crests define channels through which undesirable fluid communication is established between in-and exterior of the garment and undesirable leakage of body exudates may readily occur. Even when said crests do not lead to such serious result, the leakage barrier formed with the remarkable crests can not be uniformly brought into close contact with the wearer's skin and makes the garment uncomfortable to wear.

DISCLOSURE OF THE INVENTION

It is a principal object of the invention to solve such problems by providing a skin-contacting surface of the leakage barrier made of a soft elastic material with a corrugated configuration.

The object set forth above is achieved, according to the invention, by a disposable garment to be put against the wearer's crotch for absorption of body exudates with a crotch-contacting section comprising a liquid-permeable topsheet, a liquid-impermeable backsheet and a liquid-absorbent core disposed between these two sheets, and a pair of body exudates leakage barriers made of a soft elastic material longitudinally extending on transversely opposite sides of said crotch-contacting section on its inner surface, characterized in that a top surface of each of the leakage barriers at least partially has a corrugated configuration comprising a plurality of longitudinally alternate crests and troughs each extending transversely of the respective leakage barriers.

The leakage barriers are deformed at the respective troughs as the garment of such construction is put on the wearer's body, sufficiently to describe a smooth curve as a whole. Smoothness of curves to be described by the leakage barriers may be enhanced and formation of any remarkable crests may be avoided by increasing the number of troughs, i.e., by shortening a distance between each pair of adjacent troughs. Body exudates leakage through one or more of the troughs can be substantially avoided by appropriately selecting a height of the leakage barrier and/or by providing an arrangement such that opposite walls of each trough may tightly bear against each other and close the trough as the leakage barriers are curved.

BEST MODE FOR CARRYING OUT THE INVENTION

A garment for absorption of body exudates constructed according to the invention will be described more in detail with reference to the accompanying drawings which illustrate presently preferred embodiments.

Figure 1:
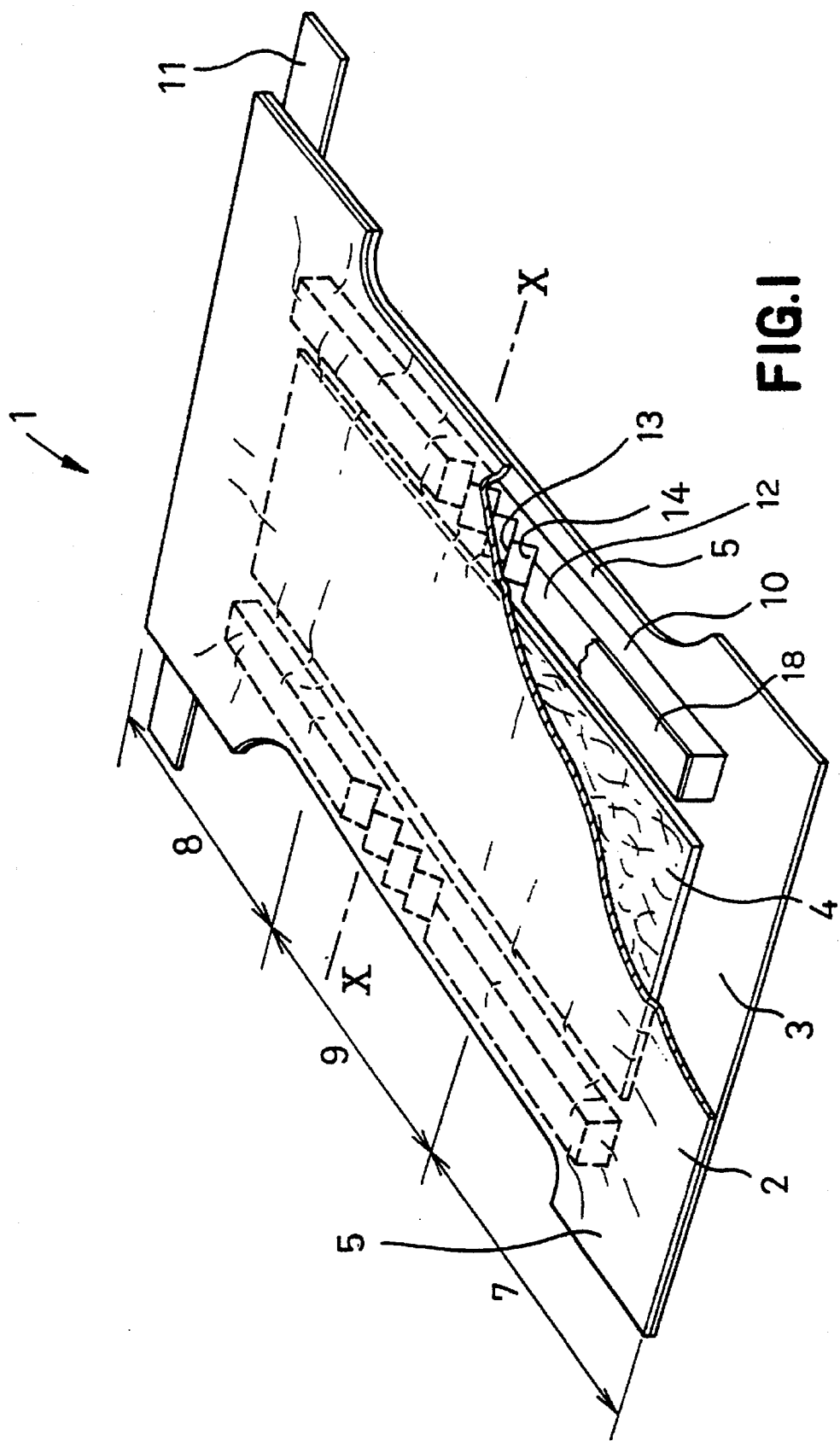
FIG. 1 is a perspective view showing a disposable diaper as partially broken away.

FIG. 1 is a perspective view showing a disposable diaper 1 as partially broken away. The diaper 1 comprises a liquid-permeable topsheet 2, a liquid-impermeable backsheet 3 and a liquid-absorbent core 4 disposed between these two sheets, wherein the top- and backsheets 2, 3 extend sideways beyond transversely opposite side edges of the liquid-absorbent core 4 and bonded together a given locations to form respective side flaps 5. The diaper 1 comprises, as viewed longitudinally thereof, a front section 7, a rear section 8 and a crotch section 9 extending between these front and rear sections 7, 8. On the respective side flaps 5, a pair of leakage barriers 10 longitudinally extend across the crotch section 9, respectively, into the front and rear sections 7, 8. Tape fasteners 11 extend outward from side edges of the respective side flaps 5 in the rear section 8. The leakage barriers 10 are soft elastics of an appropriate cross-sectional shape, e.g., a rectangular, circular or trapezoidal shape and their top surface (i.e., skin-contacting surface 4) have, at least in the crotch section 9, a corrugated configuration defined by a plurality of longitudinally alternate crests 13 and troughs 14, respectively.

Figure 2:
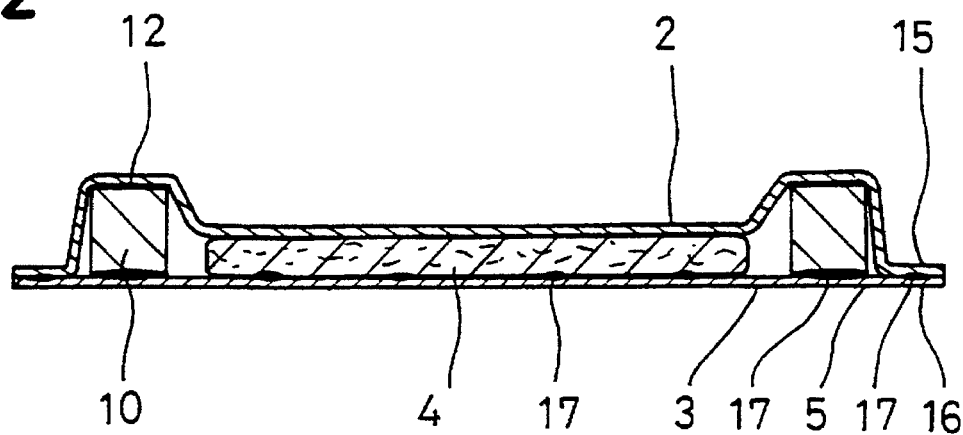
FIG. 2 is a sectional view taken along a line X—X in FIG. 1.

FIG. 2 is a sectional view taken along aline X—X in FIG. 1, showing a configuration of the crotch section 9. As shown, the top- and backsheets 2, 3 are liquid-tightly bonded together along their mutually opposed peripheries 15, 16 with use of hot melt adhesive 17. The liquid-absorbent core 4 and the leakage barriers 10 have their bottom surfaces intermittently bonded to the backsheet 3 with use of hot melt adhesive 17. It is also possible within the scope of the invention to bond the liquid-absorbent core 4 and the leakage barriers 10 to the topsheet 2, if desired.

Figure 3:
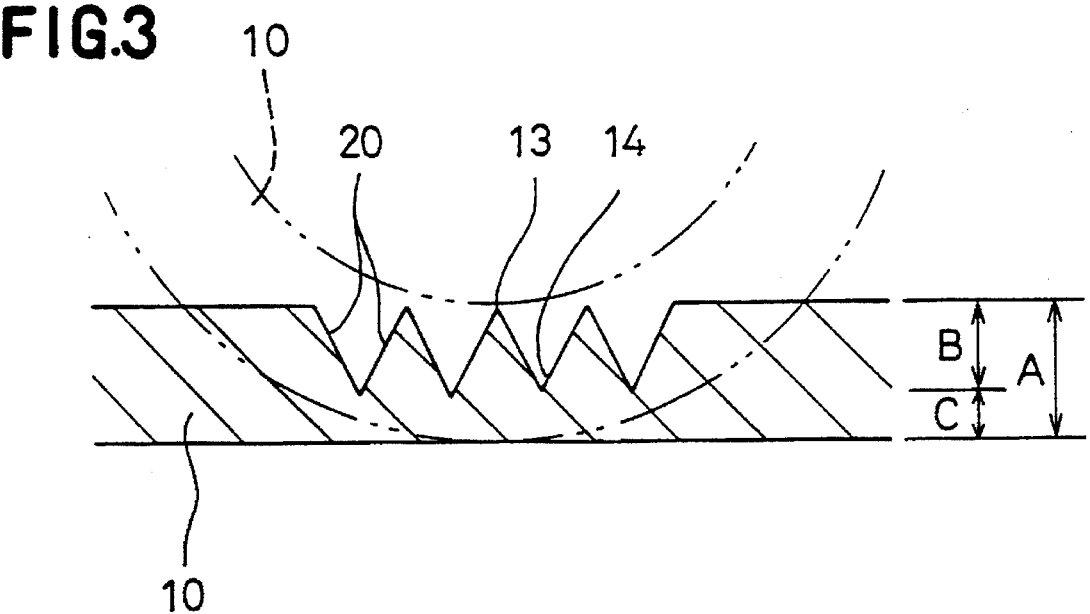
FIG. 3 is a side view showing an important portion of the leakage barrier.

FIG. 3 is a side view showing an important portion of the leakage barrier 10 wherein imaginary lines indicate the position occupied by the leakage barrier 10 when the latter is curved. Referring to FIG. 3, reference symbol "A" designates a height of the leakage barrier 10 itself, reference symbol "B" designates a depth of the trough 14 and reference symbol "C" designates a thickness of the leakage barrier 10 at the bottom of the trough 14. While these dimensions "A","B","C" as well as the configuration of the trough 14 may be appropriately selected, it is preferred to dimension the height "A" sufficient to assure that the garment can be reliably sealed against the crotch as well as around the legs of the wearer independently of a thickness selected for the liquid-absorbent core 4. The trough 14 is preferably configured so that a pair of mutually opposed walls 20 defining each trough 14 may be brought into close contact with each other and close a groove defined by the trough 14 as the leakage barrier 10 is curved in order to avoid leakage of body exudates which otherwise might occur through the trough 14, in wear of the garment to this end, the trough 14 is preferably V-shaped. However, the respective troughs 14 may function exclusively to facilitate the leakage barrier to be curved so far as the bottom thickness "C" of the leakage barrier 10 is dimensioned sufficient to avoid leakage of body exudates, in view of the fact that the leakage barrier 10 is curved in a manner dependent on a size of the wearer's body.

The leakage barrier 10 operating in the manner as has been described above may be formed by a soft elastic closed or open cell foam of a thermoplastic material such as a polyurethane or polyethylene or by a fibrous web such as a nonwoven fabric made of crimped thermoplastic composite fibers and having a strength of stability against compression. Such leakage barrier 10 may be disposed between the top- and backsheets 2, 3 as shown or bonded to the upper surface of the topsheet 2. Such leakage barrier 10 is useful not only for a disposable diaper but also for the other garments such as a sanitary napkin, training pants, a diaper for incontinence and urine absorbent pads.

Figure 4:
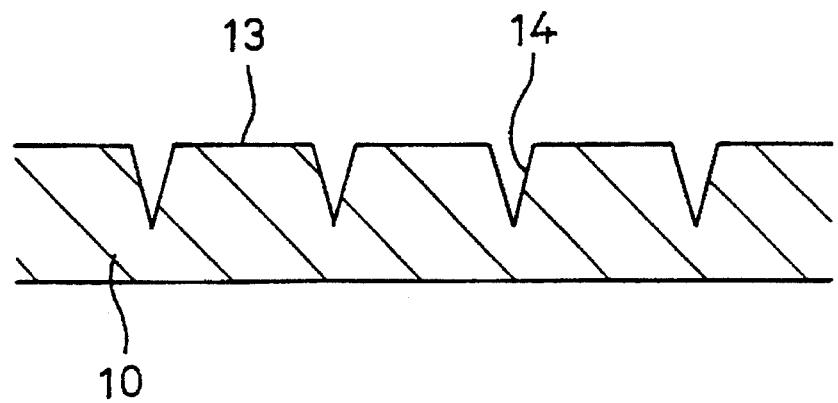
FIG. 4 is a view similar to FIG. 3 but showing an important portion of a leakage barrier modified relative to the leakage barrier of FIG. 3.

FIG. 4 is a side view showing an important portion of a leakage barrier 10 slightly modified relative to the leakage barrier 10 of FIG. 3, wherein the troughs 14 are spaced one from another. The invention may be executed also in this manner.

Components of the garment for absorption of body exudates, i.e., the top- and backsheets 2, 3 as well as the liquid-absorbent core 4 may be made of materials usually employed in this field of art.

As shown in FIG. 1, the leakage barriers 10 may be provided with longitudinally stretchable elastic members with a preselected tension to top surfaces of the leakage barriers 10 or to lower surfaces of the topsheet 2 at the location opposed to the top surfaces of the leakage barriers 10 with use of adhesive so that the leakage barriers 10 may be normally biased thereby to be curved.

With the body exudates absorbing garment of the invention, the leakage barriers are smoothly curved as the garment is put on the wearer's body and thereby comfortableness to wear is significantly improved, since the leakage barriers have on their top surface a corrugated configuration comprising a plurality of longitudinally alternate crests and troughs. Additionally, leakage of body exudates which otherwise might occur through the troughs can be substantially avoided, for example, by properly dimensioning the bottom thickness of each trough.

INDUSTRIAL APPLICABILITY

The garment according to the present invention is useful for disposable diapers, training pants and sanitary napkins. The leakage barriers of the garment are utilisable for not only the wearer's legs, but also for the wearer's waist.

We claim:

1. A disposable garment to be positioned against a wearer's crotch for absorption of body exudates with a crotch-contacting section comprising:

a liquid-permeable topsheet;

a generally flat liquid-impermeable backsheet;

a liquid-absorbent core disposed between the topsheet and the backsheet; and a pair of body exudate leakage barriers made of a soft elastic material positioned on said backsheet and longitudinally extending on transversely opposite sides on an inner surface of said crotch-contacting section, each of said leakage barriers including a plurality of longitudinally alternating crests and troughs disposed solely in said leakage barriers.

2. A disposable garment to be positioned against a wearer's crotch for absorption of body exudates with a crotch-contacting section comprising:

a liquid-permeable topsheet;

a liquid-impermeable backsheet;

a liquid-absorbent core disposed between the topsheet and the backsheet; and a pair of body exudate leakage barriers made of a soft elastic material longitudinally extending on transversely opposite sides on an inner surface of said crotch-contacting section;

wherein at least a portion of a top surface of each of said leakage barriers includes a corrugated configuration comprising a plurality of longitudinally alternating crests and troughs, each extending transversely of the respective leakage barriers, each of said troughs being configured such that, when the garment is positioned on the wearer with said leakage barriers in a curved configuration, a pair of mutually opposite walls defining each trough are brought into close contact with each other to close said trough.

3. The disposable garment of claim 2, wherein said troughs are V-shaped.

4. The disposable garment of claim 2, wherein said leakage barriers are provided with longitudinally stretchable elastic members on said top surface thereof.

* * * * *